(12) United States Patent
Andersson

(10) Patent No.: US 11,541,166 B2
(45) Date of Patent: Jan. 3, 2023

(54) INFUSION PUMP

(71) Applicant: Carucell AB, Gothenburg (SE)

(72) Inventor: Morgan Andersson, Häggenås (SE)

(73) Assignee: Carucell AB, Gothenburg (SE)

( * ) Notice: Subject to any disclaimer, the term of this patent is extended or adjusted under 35 U.S.C. 154(b) by 211 days.

(21) Appl. No.: 16/768,969

(22) PCT Filed: Nov. 25, 2018

(86) PCT No.: PCT/SE2018/051210
§ 371 (c)(1),
(2) Date: Jun. 2, 2020

(87) PCT Pub. No.: WO2019/108116
PCT Pub. Date: Jun. 6, 2019

(65) Prior Publication Data
US 2021/0038804 A1 Feb. 11, 2021

(30) Foreign Application Priority Data

Dec. 3, 2017 (SE) .................... 1751490-2

(51) Int. Cl.
*A61M 5/142* (2006.01)
*A61M 5/168* (2006.01)

(52) U.S. Cl.
CPC .... *A61M 5/14216* (2013.01); *A61M 5/16809* (2013.01); *A61M 5/16881* (2013.01)

(58) Field of Classification Search
CPC .......... A61M 5/14212; A61M 5/14216; A61M 5/16809; A61M 5/16881
See application file for complete search history.

(56) References Cited

U.S. PATENT DOCUMENTS

| 2,358,228 | A |   | 9/1944  | Hoof       |                |
|-----------|---|---|---------|------------|----------------|
| 4,121,619 | A | * | 10/1978 | Pauliukonis | F16K 31/42     |
|           |   |   |         |            | 137/493        |
| 5,188,519 | A | * | 2/1993  | Spulgis    | F04B 53/122    |
|           |   |   |         |            | 417/511        |
| 6,270,481 | B1| * | 8/2001  | Mason      | A61M 5/1424    |
|           |   |   |         |            | 604/181        |

(Continued)

FOREIGN PATENT DOCUMENTS

| DE | 4038050 A1    | 6/1992 |
|----|---------------|--------|
| WO | 2012019726 A1 | 2/2012 |

OTHER PUBLICATIONS

International Search Report and Written Opinion dated Jan. 30, 2019 in connection with PCT/SE2018/051210 filed Nov. 25, 2018.

*Primary Examiner* — James D Ponton
(74) *Attorney, Agent, or Firm* — Downs Rachlin Martin PLLC

(57) ABSTRACT

An infusion pump is disclosed. The infusion pump comprises a chamber having a distal end and a proximal end, and a longitudinal axis between the proximal end and the distal end. A piston is arranged for reciprocating movement within the chamber and along the longitudinal axis. At least one outlet is arranged from the chamber and may comprise an outlet valve. At least one inlet is provided into the chamber. The outlet and the inlet are axially spaced apart along the longitudinal axis of the chamber. A method for operating the pump is also provided.

9 Claims, 6 Drawing Sheets

(56) References Cited

U.S. PATENT DOCUMENTS

2007/0191770 A1* 8/2007 Moberg ............ A61M 5/14244
604/131
2015/0290389 A1* 10/2015 Nessel ...................... F04B 3/00
604/152

* cited by examiner

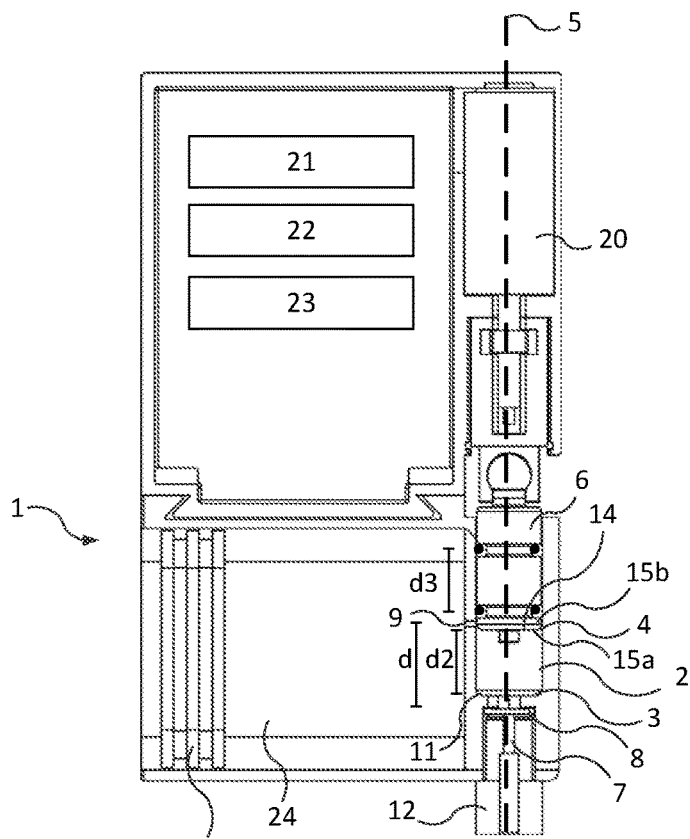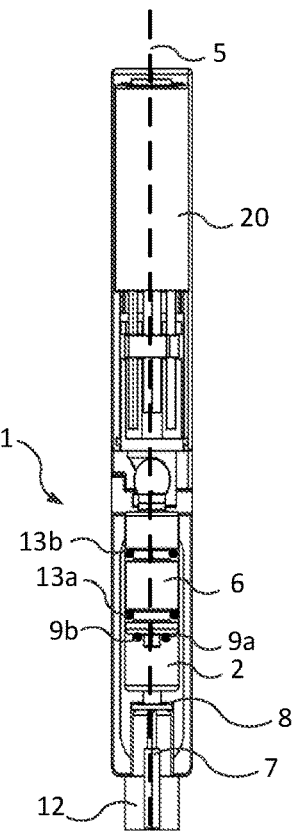
Fig. 1a    Fig. 1b
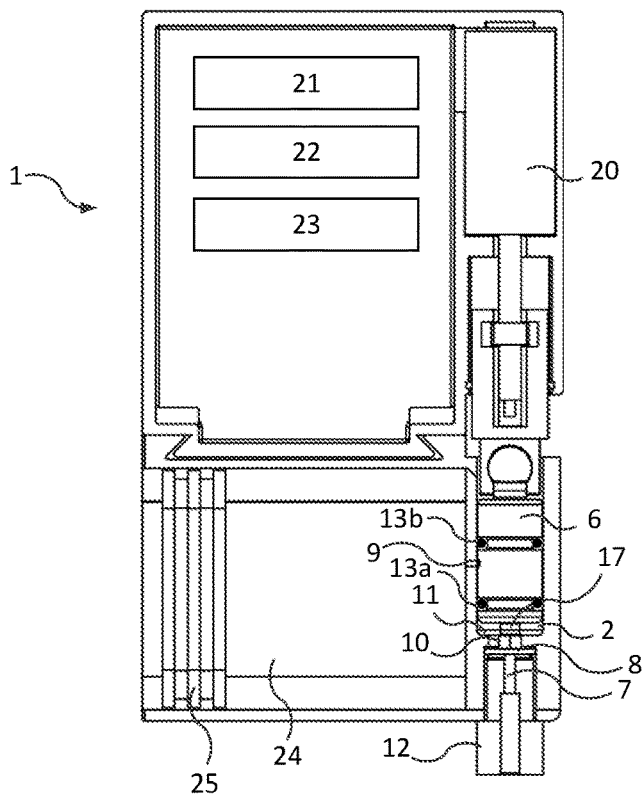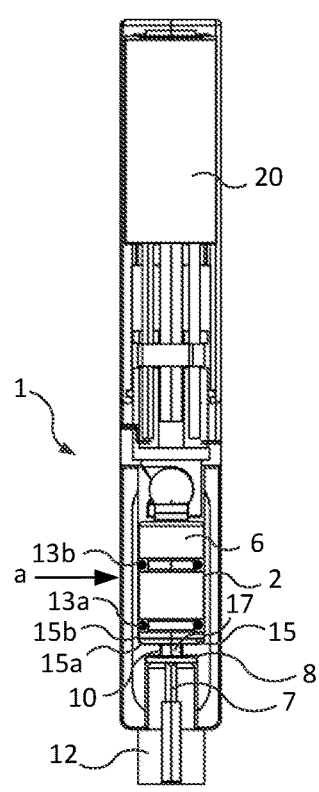
Fig. 1c    Fig. 1d

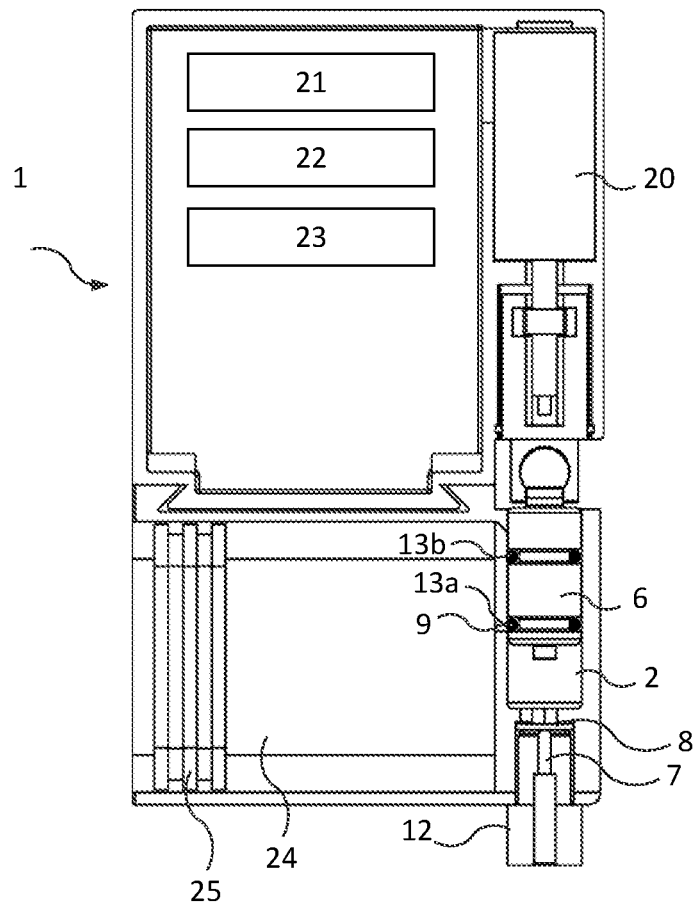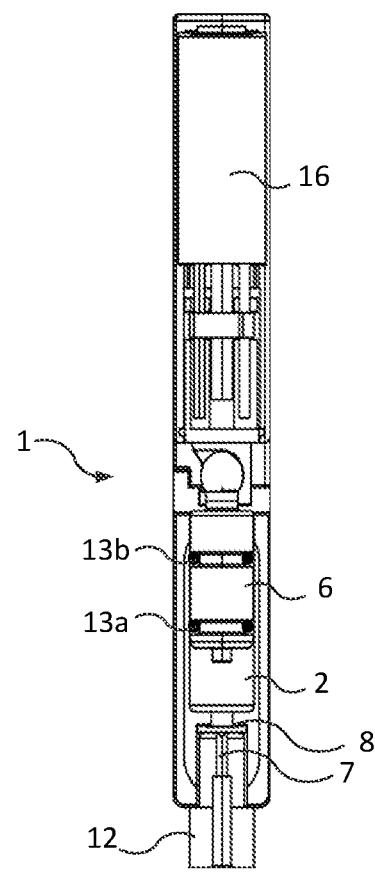
Fig. 1eFig. 1f
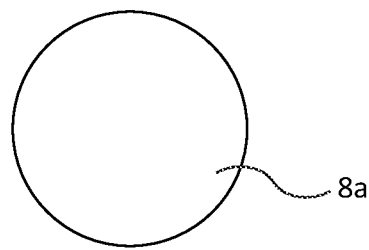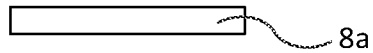
Fig. 2aFig. 2b

INFUSION PUMP

FIELD OF THE INVENTION

This invention pertains in general to the field of infusion pumps, such as ambulatory infusion pumps that may be devised for application in micro infusion therapies. More particularly, the invention relates to an infusion pump, which comprises a chamber having a distal end and a proximal end, and a longitudinal axis between the proximal end and the distal end. A piston is arranged for reciprocating movement within the chamber and along the longitudinal axis. At least one outlet is arranged from the chamber and may comprise an outlet valve. At least one inlet is provided into the chamber. The outlet and the inlet are axially spaced apart along the longitudinal axis of the chamber. Since the inlet and the outlet are axially spaced apart, the piston may acts as an inlet valve, such that access to the chamber via the inlet is not possible during a compression phase of the pump. Hence, only the outlet is exposed to the chamber during the compression phase. Thereby, a separate inlet valve at the inlet is not necessary, since the piston acts as the inlet valve. A method for operating the pump is also provided. The pump may be operated by filling and re-filling the chamber from a reservoir connected to the chamber via the inlet.

BACKGROUND OF THE INVENTION

Ambulatory infusion pumps may be used for infusion therapy of liquid medicaments or nutrients, such as for diabetes care or pain management. The devices are designed for continuous delivery of small precise amounts of the liquid. The ambulatory infusion pumps are operated by interacting with the infusion pump via a user interface including a display and buttons for manipulating the infusion pump. The devices are normally battery powered and include various electronics, and a pumping unit. The liquid is contained in a reservoir. Since the user normally carries the device around the clock, it is desired that the device is small and light. However, many times that is not the case due to the type of pump unit used and the requirements for a user interface, which restricts the possibilities to design a device that is convenient to carry and simple to operate. The design is dictated by the technology rather than user needs. However, due to the small amounts of liquid being administrated, designing a reliable pump unit that that does not dictate the design options for the device is challenging.

One example of an ambulatory infusion pump is the insulin pump. This micro infusion pump has evolved from a manual syringe. Most insulin pumps available on the marked are simply an atomized syringe comprising a cylindrical container and a piston. Movement of the piston in small increments relative the cylindrical container is effected by a small step motor in order to deliver a predefined amount of insulin at predetermined time intervals, which simulates a "continuous" delivery of insulin. The amount of insulin delivered in each incremental movement of the piston can be about 0.00025-0.00050 ml or 0.25-0.50 mm3.

Piston pumps of the type used for insulin pumps are relatively bulky. The housing for the pump unit needs space for the full stroke of the piston, which is essentially twice the entire length of the cylindrical container for the medicament. The cylindrical container has only one outlet, such that the container needs to be filled or replaced after a single stroke of the piston. The devices are designed around the technology, including the pump unit, battery and display, making them fairly bulky, square and inconvenient for the user to carry. Devices containing this type of technology tend to be inconvenient for the user. The pump unit offers few options to design a user-friendlier device.

Another example of an infusion pump is for administration of a medicament for pain management or for nutrients. Such pumps may deliver medication or nutrients from either a cassette type of tube arrangement or from an administration type of tube arrangement. Such pumps include a reusable control module detachably coupled to a pressure plate at a top surface of a disposable fluid reservoir cassette. Fluid is pumped from the cassette by the reusable control module when the cassette is coupled to the control module. These types of pumps tend to be less precise, making them unsuitable for administration of minute amounts of liquid, such as insulin.

Still other examples of infusion pumps comprise a flow material reservoir wherein the liquid is pressurized. The liquid is contained in a compressible container or bag, and air around the container or bag is pressurized. These devices are complex and expensive, e.g. including sensors to measure the volume of the flow material reservoir and/or the volume of flow material dispersed from the infusion pump.

Hence, an improved infusion pump, and components useable for such an improved infusion pump, would be advantageous and in particular allowing for improved robustness, increased flexibility, cost-effectiveness, and/or reduced complexity would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an infusion pump as defined by the claims.

Embodiments include an infusion pump comprising a chamber, e.g., having a distal end and a proximal end, and a longitudinal axis between the proximal end and the distal end; a piston arranged for reciprocating movement within the chamber and along the longitudinal axis; at least one outlet from the chamber, e.g having an outlet valve; and at least one inlet into the chamber.

Hence, embodiments may provide a valve system comprising an inlet, an outlet, an outlet valve, and a piston operating as an inlet valve. During reciprocating movement of the piston and in different positions within the chamber, it may close the inlet such that liquid in the chamber is pressurized and the outlet valve opened, generate vacuum in the chamber to close the outlet valve while the inlet is not exposed to the chamber, and exposed the inlet such that it is open into the chamber and liquid may fill the chamber.

The outlet and the inlet may be axially spaced apart along the longitudinal axis of the chamber. The piston may be configured to provide an inlet valve and a pressure generating component as a single member.

The infusion pump may be operable with a compression phase, during which fluid in the chamber is delivered through the outlet, and a re-filling phase, during which the chamber is re-filled with fluid through the inlet. The piston has at least one axial position within the chamber overlapping an axial positon of the inlet into the chamber in the delivery phase to prevent fluid to enter into the chamber. Hence, the piston may provide or act as an inlet valve being closed during the delivery phase and being open or opening the inlet at least partially during the re-filling phase. The inlet valve may be closed when the piston is in the axial position within the chamber overlapping the axial positon of the inlet.

The infusion pump may be operable with a re-filling phase, during which the chamber is re-filled with fluid through the inlet. The piston may have at least one other axial position within the chamber at least partially non-overlapping the axial position of the inlet in the chamber. The inlet in the other axial position of the piston may be at least partially exposed to the chamber in the re-filling phase to allow fluid to enter into the chamber. Hence, the piston may provide or act as an inlet valve being open or opening the inlet at least partially during the re-filling phase when non-overlapping the axial position of the inlet in the chamber.

In a first time period of the re-filling phase, the outlet valve may be closed and the piston may axially overlap the inlet to build vacuum in the chamber during movement of the piston towards the proximal end. In a second time period of the re-filling phase, the piston may be at least partially axially non-overlapping the inlet, wherein the inlet is open into the chamber.

The chamber may be cylindrical. The outlet may be axially arranged at the distal end of the chamber. The inlet may be axially arranged at a side surface of the chamber, preferably at the proximal end of the chamber.

The at least one inlet may comprise a plurality of inlets. The plurality of inlets may be radially spaced apart within or around the circumference or side surface of the chamber. The plurality of inlets may be axially aligned within or around the circumference or side surface of the chamber.

The piston may comprise at least one sealing member arranged to provide a seal between the piston and the side surface of the chamber. The piston may comprise a plurality of sealing members axially spaced apart and arranged to provide a seal between the piston and the side surface of the chamber. The plurality of sealing members may comprise a first sealing member and a second sealing member. The axial distance between the first sealing member and the second sealing member may be larger than the maximum movement of the piston within the chamber. Hence, leakage from the inlet is prevented during the entire stroke of the piston.

The first sealing member may be axially positioned distal of the inlet in a delivery phase of the infusion pump. The second sealing member may be axially positioned proximal of the inlet in a delivery phase of the infusion pump. The first sealing member and the second sealing member may at least partly be axially positioned proximal of the inlet during a re-filling phase of the infusion pump.

The piston may have an end surface with a beveled circumference. The beveled circumference may be axially aligned with the inlet during the re-filling phase of the infusion pump.

Embodiments provide a method for operating an infusion pump having a chamber with a distal end and a proximal end, and a longitudinal axis between therebetween; a piston arranged for movement within the chamber and along the longitudinal axis; at least one outlet from the chamber, optionally having an outlet valve; and at least one inlet into the chamber; the outlet and the inlet being axially spaced apart along the longitudinal axis. The method may comprise axially positioning the piston within the chamber to overlap the inlet in a delivery phase of the infusion pump. The method may also comprise axially positioning the piston to at least partly to non-overlap the inlet in a re-filling phase of the infusion pump. Hence, the method may comprise operating the piston as an inlet valve and to close the inlet with the piston during a delivery phase and to open the inlet with the piston at least partially during a re-filling phase.

Embodiments comprise a computer program product with software instructions stored in a computer readable memory and being executable by a processor or controller. The computer program product may be configured to execute the method of embodiments of the invention when run by the processor or controller.

Further embodiments of the invention are defined in the dependent claims.

Embodiments of the invention provide for infusion pump that may have reduced size and reduced complexity. Embodiments of the invention also provide for a reliable infusion pump. Particularly, embodiments provide a reliable infusion pump that has a chamber that may be re-filled without the risk of fluid flowing back into the chamber. Also, the piston may act as an inlet valve, wherein the number of components and complexity is reduced. This is provided by the inlet and the outlet being axially spaced apart and having the outlet valve provided at the outlet, such as in an outlet channel, whereas only the outlet and not the inlet is exposed to the chamber during a compression phase of the pump. The inlet may be exposed at least partially at some point during a refilling phase of the pump.

Embodiments of the invention also provide a less complex and more flexible infusion pump that accurately can deliver minute volumes of fluid. Embodiments provide for precision that is sufficient for use as an insulin pump. Embodiments provide an insulin pump with a chamber that is smaller than the reservoir in which the fluid to be administered is contained. This provides for less space required for a reciprocating piston, wherein the overall foot print of the pump is reduced. Also, a smaller chamber with reduced diameter can have a piston that travels a longer distance compared to a larger chamber for delivery of the same amount of liquid. This allows other components to be smaller and/or have a smaller capacity, such as a motor, gears connecting the motor to the piston, etc. which also contributes to making the overall footprint smaller. In some embodiments, the gears may be entirely eliminated. Furthermore, enabling re-filling of the chamber provides for making the total stroke of the piston shorter for any given volume compared to delivery of the same given volume with a single stroke, as is conventional, which reduces the space required to accommodate the full stoke of the piston. With embodiments presented herein, the diameter as well as the length of the chamber can be reduced since it may be re-filled, wherein size may be reduced and accuracy improved. This all contributes to making the pump less complex and reducing the size of the pump.

Embodiments have an inlet to and an outlet to/from the chamber, which provide for pressurizing the fluid in the chamber but not in the reservoir. The embodiments allow for using the same components of the pump for refilling the chamber with fluid from the reservoir and for pressurizing the fluid in the chamber, particularly the piston doubling as a valve and a pressure generating component. This allows for reduced complexity. Also, the chamber and the reservoir can be separated, which offers increased flexibility to design a user-friendly ambulatory infusion pump that is less dependent on the technology. The chamber, which has a fixed shape, can be made much smaller than chambers of convention piston pumps operating with a single stroke. The reservoir from which the fluid is drawn can have an arbitrary shape, such as adapted to the exterior chassis of the device. The chassis can in turn be designed with the user needs in mind rather than being dictated by the pump technology. The device can for example be designed for different user groups, such as for men, women, kids etc. with different designs of the chassis where the reservoirs for different user groups have different shapes in order to accommodate requirements on the chassis design. Yet, the design of the infusion pump unit with the chamber may be fixed, but due to its small size it does not impair the flexibility and design options for the chassis. Furthermore, embodiments provide for reduced complexity that provide for overall simplified production with associated reduced manufacturing costs. Embodiments of the invention contribute to make the infusion pump precise for delivery of minute amounts of fluid, such as various aspects of valves and/or disc springs for an inlet and/or an outlet to/from the chamber. Such embodiments may form separate inventions, but each contribute and combine to the reduced complexity and increased flexibility of the infusion pump of the present invention. For example, the valve is particularly useful for an infusion pump, wherein minute amounts of a fluid are delivered. The chamber of the pump for pressurizing the fluid can be made smaller than is previously known since using the valve allows for refilling the chamber. A smaller chamber allows for a smaller diameter of a piston for pressurizing the fluid, which in turn means that the accuracy of the infusion pump is improved. The piston can simply travel a longer distance for each delivery of fluid compared to previously know infusion pumps with a single stroke, which must have a larger diameter and a shorter distance of travel to deliver the same amount. A longer travel is easier to control, allowing for improved accuracy.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIGS. 1a-1f are front and side cross-sectional views of the pump with the piston in a proximal, distal, and intermediate, respectively, positon within the chamber;

FIGS. 2a-2b is a top view and a side view, respectively, of a diaphragm valve;

DESCRIPTION OF EMBODIMENTS

Figure 3:
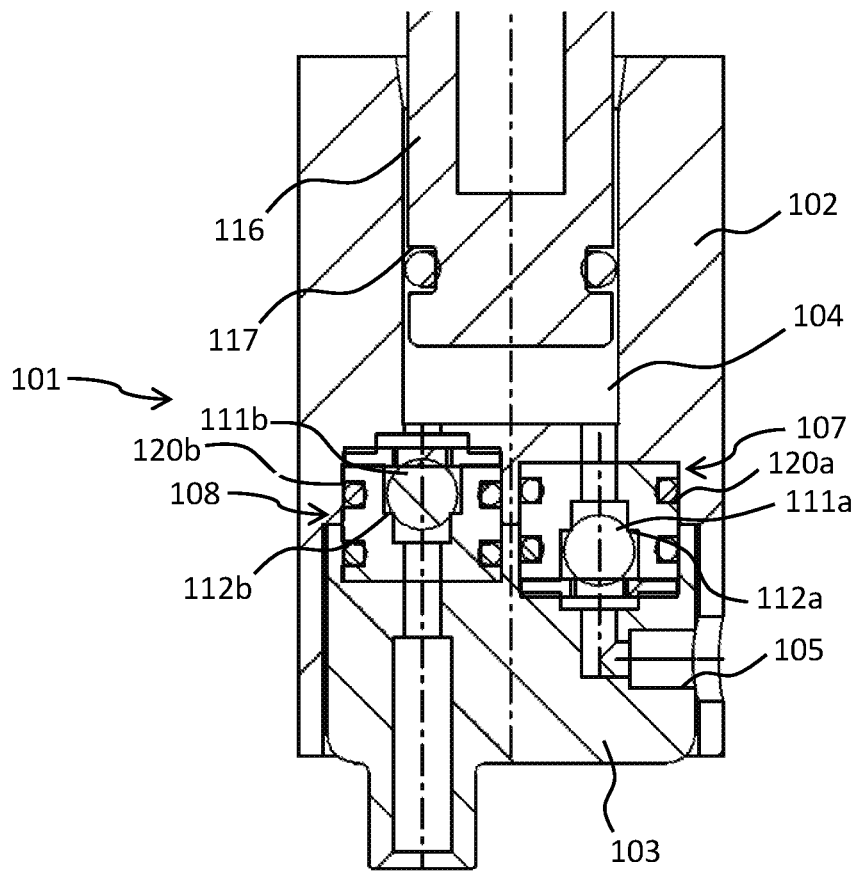
FIG. 3 is a cross-sectional view of an embodiment of the infusion pump.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable as an infusion pump 1. The infusion pump may be an ambulatory infusion pump, such as an insulin pump. However, it will be appreciated that the invention is not limited to this application but may be applied for administration of other fluids, such as liquid medicaments, liquid pain management and/or nutrient. It is particularly useful for incremental administration of minute amounts of liquid, such as about 0.00010-00050 ml in each step.

FIGS. 1a-1f illustrate embodiments of the infusion pump 1. In the following reference will be made simply to a pump 1 when referring to the infusion pump. The pump comprises a chamber 2 having a distal end 3 and a proximal end 4. A longitudinal axis 5 is defined between the proximal end 4 and the distal end 3. A piston 6 is arranged for movement, such as reciprocating movement, within the chamber 2 and along the longitudinal axis 5. The pump comprises at least one outlet 7 from the chamber 2. The outlet 7 may comprise an outlet valve 8. Also, the pump comprises at least one inlet 9, 9a, 9b into the chamber. The outlet 7 and the inlet 9, 9a, 9b are axially spaced apart along the longitudinal axis 5. The inlet may connect the chamber 2 to a reservoir 24.

The outlet 7 and the inlet 9 may be spaced apart a distance d, measured from the axial position of the outlet valve 8 to the axial position of center of the inlet 9 along the longitudinal axis 5. The distance d may be in the range of 3-20 mm, such as 4-10 mm, preferably 4-8 mm. Such a distance provides sufficient generation of vacuum in the chamber 2 for efficient re-filling of fluid into the chamber 2, as will be discussed below, while still not providing too much resistance for a motor 20 such that it may not reciprocate the piston 6. The distance d is also dependent on the force provided by the motor 20, which is connected to the piston for reciprocating movement of the piston 6. The larger distance d, the greater force required by the motor 20. Hence, for applications wherein the infusion pump is battery powered, the distance d tend to be smaller such that the motor 20 requires less energy may for building vacuum in the chamber 2. The motor 20 may be connected to the piston 6 by a releasable connection, such as a snap fit connection, e.g. a ball and socket connection as illustrated in FIGS. 1a-1f. The ball may be provided at a proximal end of the piston 6, and the socket at the distal end of an actuator of the motor 16.

As can be seen in FIGS. 1c-1d, the outlet valve 8 may be arranged in an outlet path, such as between an outlet opening 10 at a distal end surface 11 of the chamber 2 and a connector 12 or plug member. The connector 12 or plug member may e.g. be configured to connect an infusion set or other hose for discharging a fluid from the pump 1. The plug 17 may also be configured to arrange the outlet valve at a predetermined position.

The outlet valve 8 may comprise a check valve, a clack valve, a non-return valve, a reflux valve, or one-way valve. The outlet valve 8 is configured to allow fluid, such as liquid, to flow through it in only one direction. In some embodiments and as illustrated in FIGS. 1a-1f, the outlet valve 8 is a check valve. The check valve may be a diaphragm check valve, which is illustrated in FIGS. 1a-1f, and in FIGS. 2a-2b. The diaphragm check valve may comprise a flexing diaphragm positioned to create a closed valve during the re-filling phase of the pump 1. The diaphragm may be made of a medical grade elastic material with a shape that conforms to the shape of a valve seat. During the re-filling phase, the pressure on the upstream side of the chamber 2 is greater than the pressure on the downstream side within the chamber 2, which is known as the pressure differential. Once positive pressure stops, the diaphragm automatically returns to its closed position. Stopping of the positive pressure is provided by reciprocating the piston 6 back towards the proximal end of the chamber 2, which closes the outlet valve 8 when vacuum is built in the chamber 2 by movement of the piston 6 towards the proximal end 4 of the chamber 2. The diaphragm valve may abut the valve seat in the closed position. The valve seat may be circumferential surface arranged at the outlet 7, such as around the outlet path or at a distal side of the outlet opening 10. Hence, the outlet opening 10 may have a smaller diameter than the outlet path 7 providing the valve seat, as can be seen in FIGS. 1a-1f. The circumferential surface may have width. The width should be sufficient such that the outlet valve may abut thereto in order to provide a seal and close the outlet during the re-filling phase while vacuum is generated in the chamber 2.

The piston 6 is arranged to be moveable from the proximal end 4 or a proximal position of the piston 6 in the chamber 2, towards the distal end 3 or distal position of the piston 6 within the chamber 2. Proximal is referred to as the end of the chamber 2 at which the piston initiate generation of positive pressure, and distal is referred to as the end at which the piston 6 stops generating positive pressure. In the proximal position of the piston 6, illustrated in FIG. 1a, the chamber 2 may be filled with fluid while the inlet is open into the chamber 2. The pump 1 is operable with a compression phase, during which fluid in the chamber 2 is delivered through the outlet 7. In the delivery phase where positive pressure is generated, the piston 6 has at least one first axial position within the chamber 2 overlapping an axial positon of the inlet 9, 9a, 9b into the chamber 2. Such first axial positions where the piston 6 overlaps the inlet 9, 9a, 9b are illustrated in FIGS. 1c-1f. The first axial positions prevent fluid to enter into the chamber 2. Hence, the piston 6 acts as an inlet valve being closed.

The pump 1 may be operable with a single stroke of the piston 1. However, in some embodiments, it may be desired to re-fill the chamber before another delivery phase begins. Hence, the pump 1 may be operable with a re-filling phase, during which chamber 2 is re-filled with fluid through the inlet 9, 9a, 9b. The piston 6 has at least one second axial position within the chamber 2 at least partially non-overlapping the axial position of the inlet 9 in the chamber 2, such as illustrated in FIGS. 1a and 1b. In the second axial position, the piston 6 may be positioned to at least partially expose the inlet 9, 9a, 9b to the chamber 2. The piston 6 may be position in the second axial position during fraction of a filling and/or the re-filling phase to allow fluid to enter into the chamber 2. Hence, the piston 8 acts as an inlet valve being open. The piston may be in its proximal most position in the filling and/or re-filling phase. When the chamber 2 is filled/re-filled, the piston 6 may first be moved towards the distal end 3 of the chamber 2 to generate positive pressure, which closes the inlet.

The piston 6 may be moveable from the first position(s) to the second position(s) by reciprocating movement of the piston within the chamber 2 from the proximal end 4 towards the distal end 3 and back to the proximal end 4. In a first time period of the re-filling phase, the outlet valve 8 is closed and the piston 6 is axially overlapping the inlet 9 to build vacuum in the chamber 2. This is illustrated by the positions of the piston in FIGS. 1c and 1d. The piston is in its distal most position in FIG. 1d, and has moved slightly in the proximal direction in FIG. 1c, which initiates building vacuum and closing the outlet valve. Vacuum may build during movement of the piston 6 towards the proximal end 4, e.g. from the position illustrated in FIG. 1d to the position illustrated in FIG. 1c. In a second time period of the re-filling phase, the piston 6 is at least partially axially non-overlapping the inlet 9, such as illustrated with the position of the piston 6 in FIGS. 1a and 1b. The inlet 9 may be open in the range of 1-10 seconds, such as 1-5 second, preferably 2-3 seconds, before the piston 6 is moved towards the distal end 4 of the chamber 2 to close the inlet, as is illustrated in FIGS. 1e and 1f.

As can be seen in FIG. 1c-1d, the distal end of the piston 6 may comprise plug 17 or end member having reduced diameter compared to the maximum diameter of the piston 6. When the piston is in the distal most position within the chamber 2, the plug 17 is received in the outlet opening 10, which may have a diameter only slightly larger than the plug such that the latter is received snugly therein. This provides for rapid buildup of vacuum and closing of the outlet seal, e.g. by the diaphragm valve rapidly seating against the valve seat. The outlet valve 8 may be closed when the plug or end member exits the outlet 10 of the chamber 2, as is illustrated in FIG. 1c.

The chamber 2 may be cylindrical, such as circular cylindrical. In other embodiments, the chamber 2 is elliptical cylindrical. This allows for movement of the piston 6 in the chamber with low friction against the side surfaces of the chamber 2. Furthermore, the outlet 7 may be axially arranged at the distal end 3 of the chamber 2, or at a distal end of an effective length d2 of the chamber, as is illustrated in FIG. 1a. The effective length is the maximum length between a distal end surface 11 of the chamber 2 and distal end surface of the piston 6 when the piston is in its proximal or start position, such as illustrated in FIG. 1a. The inlet 9 may be axially arranged at a side surface of chamber 2, preferably at the proximal end of the chamber 2. Arranging the inlet 9 at the proximal end of the chamber provides for filling the chamber 2 when the piston 6 is at or close to a proximal end position. This in turn means that when the delivery phase begins, the piston 6 will quickly overlap the inlet, preventing fluid from returning through the inlet 9 and pressure to be increased in the chamber 2 allowing fluid to be discharged. Hence, this contributes to the reliability and safety of the pump 1. The wall(s) of the chamber may continue proximally beyond the proximal end of the chamber 2 to provide a seal and/or guide the piston 6.

FIG. 1b illustrates the at least one inlet 9, 9a, 9b. In some embodiments, a single inlet 9 is provided. In embodiment illustrated in FIG. 1b, the at least one inlet comprises a plurality of inlets 9a, 9b, such as two or three. A plurality of inlets may also be provided in the other embodiments presented herein. In FIG. 1b, the inlets are illustrated with enlarged size and slightly moved towards the distal end of the chamber 2 for explanatory purposes. They may be positioned axially as indicated by the inlet 9 of FIG. 1a. Even more than three inlets may be provided. Providing a plurality of inlets provides for decreasing the area of each inlet 9a, 9b. This may be useful for avoiding damaging a sealing member while passing over the inlets 9, 9a, 9b. It is also useful for efficiently refilling of the chamber 2 and in order to reducing the time required to expose the inlet 9, 9a, 9b to the chamber 2.

The plurality of inlets 9, 9a, 9b may be radially spaced apart within the chamber 2, as is illustrated in FIG. 1b. Hence, the inlets 9, 9a, 9b may be arranged at separate radial positions around the side surface of the chamber 2. In some embodiments, the inlets 9, 9a, 9b are axially aligned within the chamber 2, i.e. provided at the same axial height at the side surface of the chamber 2. In other embodiments, at least two of the inlets 9, 9a, 9b are provided at different axial heights within the chamber 2.

As is illustrated in FIGS. 1a-1f, the piston 6 may comprise at least one sealing member 13a, 13b. The sealing member 13a, 13b may be arranged to provide a seal between the piston 6 and the side surface of the chamber 2. The sealing member 13a, 13b may comprise an O-ring. However, in other embodiments, the sealing member is formed as a monolithic section of the piston 6, i.e. formed integral therewith. In some embodiments, the piston 6 and the monolithic section are made of the same or separate material, where the sealing member 13a, 13b is formed as a flange, e.g. being flexible, and having a diameter substantially equivalent or slightly larger than a diameter of the chamber 2. In other embodiments, the sealing member 13a, 13b is formed by a side surface of the piston 6, which has a precision fit in the chamber 2. If the dimension of the side surface of the piston 6 and the side surface of the chamber 2 are close enough, a seal between the surfaces is provided. A seat for the sealing member 13a, 13b may be provided in the piston 13, such as is illustrated in FIGS. 1a-1f. A sealing member is particularly useful for applications where the positive pressure in the chamber 2 is low, such as when the pump 1 is designed as an insulin pump.

As mentioned above, in embodiments where the sealing member 13a, 13b has a dimension being larger than a diameter of the chamber 2, the sealing member 13a, 13b may be damaged in case the area of the inlet 9, 9a, 9b is too large. Providing a plurality of inlets 9a-9c, each with a smaller area but with a total area equivalent to an inlet with a larger area, prevents the risk of such damage, effectively proving a more reliable pump 2. The diameter of the inlet may be in the range of 0.2-2 mm, such as 0.5-1 mm.

As illustrated in FIGS. 1a-1f, the piston 6 may comprise a plurality of sealing members 13a, 13b. The plurality of sealing members 13a, 13b may be axially spaced apart. The plurality of sealing members 13a, 13b may be arranged to provide a seal between the piston 6 and the side surface of the chamber 2 at separate axial positions. For example, the plurality of sealing members 13a, 13b may comprise a first sealing member 13a and a second sealing member 13b. The axial distance d3, illustrated in FIG. 1a, between the first sealing member 13a, and the second sealing member 13b may be larger than the maximum reciprocating movement or the full stroke of the piston 6 within the chamber 2. The first sealing member 13a may be axially positioned distal of the inlet 9, 9a, 9b in the delivery phase of the pump 1, as is illustrated in FIGS. 1b-1f. The first sealing member 13a and the second sealing member 13b are at least partly axially positioned proximal of the inlet 9, 9a, 9b during the re-filling phase of the pump 1. This is illustrated in FIGS. 1a-1b where the first sealing member 13a is partly axially positioned proximal of the inlet 9, 9a, 9b and the second sealing member 13b is completely axially positioned proximally of the inlet 9, 9a, 9b. The second sealing member 13b may be axially positioned proximal of the inlet 9, 9a, 9b also in the entire delivery phase of the pump 1, as illustrated in FIG. 1d with arrow a, wherein the piston 6 is in the distal most position and the second sealing member 13b is located proximal of the location of the inlet 9, i.e. at arrow a. Hence, fluid is prevented from leaking to the exterior between the piston 6 and the side surface of the chamber 2.

As illustrated in FIGS. 1a and 1d, the piston 6 may comprise an end surface 14 with a beveled circumference 15 toward the side surface of the piston 2. The beveled circumference 15 may be axially aligned with the inlet 9 during the re-filling phase of the infusion pump. A distal end 15a of the bevel may be positioned at a distal portion of the inlet 9 during the re-filling phase, or even slightly distal of the distal portion of the inlet 9, as is illustrated in FIG. 1a. A proximal end 15b of the bevel 15 may be positioned at a proximal portion or at the center of the inlet 9 during the re-filling phase. Hence, fluid may efficiently pass the bevel 15 to re-fill the chamber 2. When the delivery phase commences, the inlet 9 may be quickly closed, as is illustrated in FIG. 1e, wherein the first sealing member 13a is positioned at least partially distal of the distal most portion of the inlet 9. Hence, this contributes to the reliability and efficiency of the pump 1. The chamber 2 may have a bevel at the intersection of its side surface and distal end surface, as is illustrated in FIG. 1d. The shape of the bevel 15 of the piston 6 may substantially conform to the shape of the bevel at the intersection. This contributes to efficiently emptying of the chamber and building vacuum in therein. It also contributes to efficient and reliable production of the components with a precise fit.

The piston 6 may be connected to a motor 20 for moving the pump 1. The motor 20 may be controlled by a processor 21 running a computer program stored in a memory 22 of the pump 1. The motor 20 may comprise a step motor or a piezo electric motor. A piezo electric motor is particularly useful for moving the piston in small increments at discrete time intervals, such as used for an insulin pump. A piezo electric motor can maintain the piston 6 in a fixed position without any holding current. This is particularly useful in a battery charged device, such as an ambulatory infusion pump. Furthermore, a piezo electric motor may operate without a gearbox to move the piston in small increments. For a step motor to provide the same force at the same small increments, a gearbox may be required. For the same force provided by the motor, a piezo electric motor is more compact. This is particularly useful with the pump 1 of the embodiments herein where vacuum is generated, requiring sufficient force to return the piston 6. Hence, fewer components are required with a piezo electric motor, contributing to the reliability of the pump 2. It also contributes to making the pump compact due to its small size, which also is advantageous for ambulatory pumps. The pump 1 may also comprise a battery 23 and a circuitry for wireless communication of data. Hence, the pump does not require a user interface for providing settings for the device. Data for operating the device may thus be communicated from a remote device, such as a smart phone. This contributes to the compactness of the pump 1, making it more convenient to use.

The piston 6 with associated parts, the chamber 2, the inlet, the outlet 7, the outlet valve 8, the reservoir 24, and optionally the connector 12 or another member fixing the outlet valve 8 in the predetermined position, may be provided as a cassette. Hence, the motor 20, the processor 21 or controller, the memory 22, the battery 23 and other electronic components may be for multiple use. The cassette may be single use. The reservoir 24 may be collapsible, and optionally prefilled. Hence, the reservoir may collapse as liquid is drawn into the chamber 2. In other embodiments, such as illustrated in FIGS. 1a-1f, the reservoir 24 may comprise a piston 25, which moves towards the inlet 9 as liquid is delivered into the chamber 2. A seal may be provided between a wall of the reservoir and the piston 25. Alternatively, the reservoir 24 is a collapsible bag, which may be positioned within a casing.

Embodiments provide a method for operating the pump 1. The method comprises axially positioning the piston 6 within the chamber 2 to overlap the inlet 9 in the delivery phase of the pump 1, as illustrated in FIGS. 1e-1f. Optionally, the method may comprise axially positioning the piston 6 within the chamber 2 to overlap the inlet 9 during an initial phase of the filling or re-filling phase of the pump 1, as illustrated in FIGS. 1c-1d. The method also comprises axially positioning the piston 6 to at least partly non-overlap the inlet 9, 9a, 9b during a second phase of the re-filling phase of the pump 1, as is illustrated in FIGS. 1a-1b. The method may comprise further steps, as defined with regard to the description of embodiments of the pump 1. The method may be used to prime the pump before actually being used. Also, the method is useful for delivery of other fluids than medicaments.

A computer program product may be stored in a computer readable memory, such as memory 22. The computer program may be executable by a controller, such as processor 21. The computer preprogram product may be configured to execute the method of embodiments described herein when run by the controller.

FIGS. 2a-2b illustrate an embodiment of a diaphragm valve 8a. The diaphragm valve 8a may be arranged as the outlet valve 8 illustrated in FIGS. 1a-1f and may comprise an elastic material. This provides for efficient sealing against the valve seat. The diaphragm valve 8a may be arranged between the valve seat and the connector 12. Hence, the valve seat and a proximal end surface facing the valve seat may be spaced apart a distance slightly larger than the thickness diaphragm valve 8a. The width of the diaphragm valve 8a may be slightly smaller than the width of the space between the valve seat and the connector 12. Also, the width of the diaphragm valve 8a is larger than the width of the outlet 10 of the chamber 2. Hence, when positive pressure is generated, the diaphragm valve 8a is moved towards the connector 12, whereby the outlet valve is opened. When negative pressure is generated the diaphragm valve 8a is moved towards the valve seat, whereby the outlet valve is closed. The distance between the proximal end surface of the connector and the valve seat may be less than the length of the plug 17. This provides for efficient closing of the outlet valve 8 before the plug leaves the outlet 10 of the chamber 2 by rapid buildup of vacuum. Hence, this increases the efficacy as well as the safety of the pump since fluid may not return into the chamber 2.

FIG. 3 illustrates components of embodiments of an infusion pump unit, which will be referred to as an infusion pump in the following. The infusion pump comprises a housing 100. In the embodiment of FIG. 3, the housing comprises a first housing unit 102 and a second housing unit 103. A chamber 104 is located at least partially in the first housing unit 102. The housing 100 includes an outlet 105, and an inlet 106. An outlet valve 107 may be arranged between the chamber 104 and the outlet 105. An inlet valve 108 may be arranged between the inlet 106 and the chamber 104. However, the outlet valve 107 and the inlet valve 108 may be axially spaced apart along the longitudinal axis of the chamber 104, according to the principles described above with regard to FIGS. 1a-1f. The inlet valve 108 may be arranged in the inlet 9 of the embodiments of FIGS. 1a-1f and used in addition to or replace the piston acting as the inlet valve.

Figure 4:
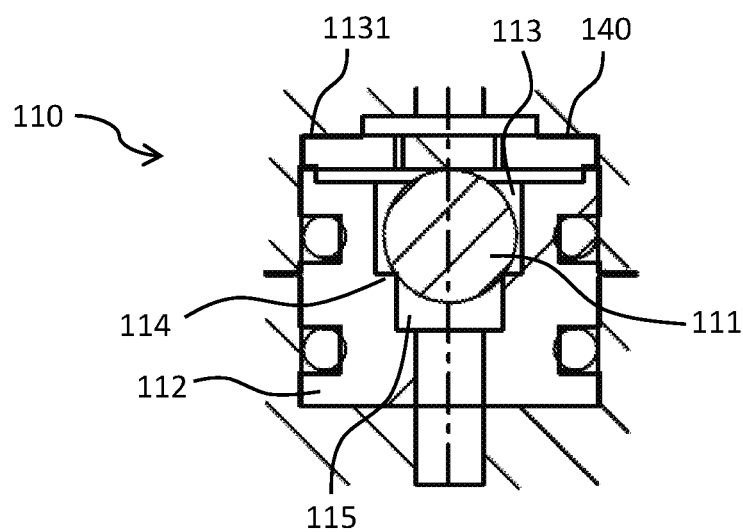
FIG. 4 is a cross-sectional view of an embodiment of a valve.
Figure 10A:
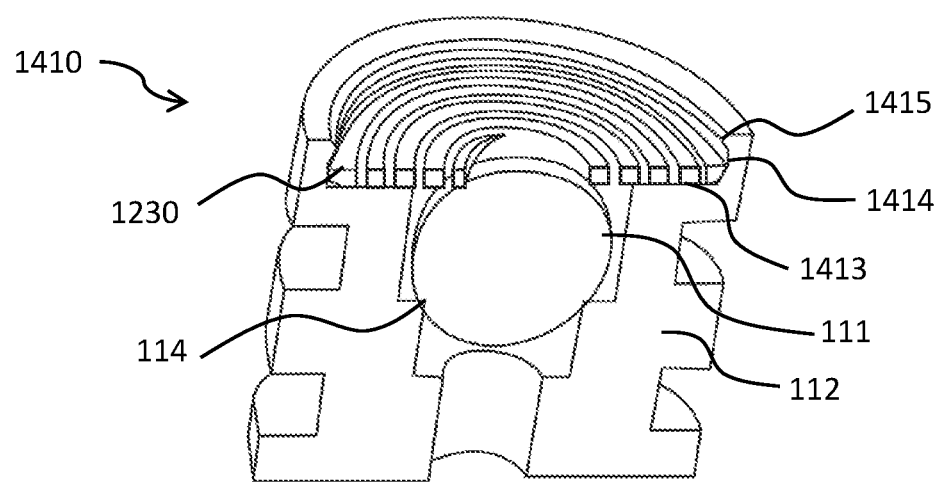
FIG. 10a is a cross sectional view of a pre-assembled valve.
Figure 10B:
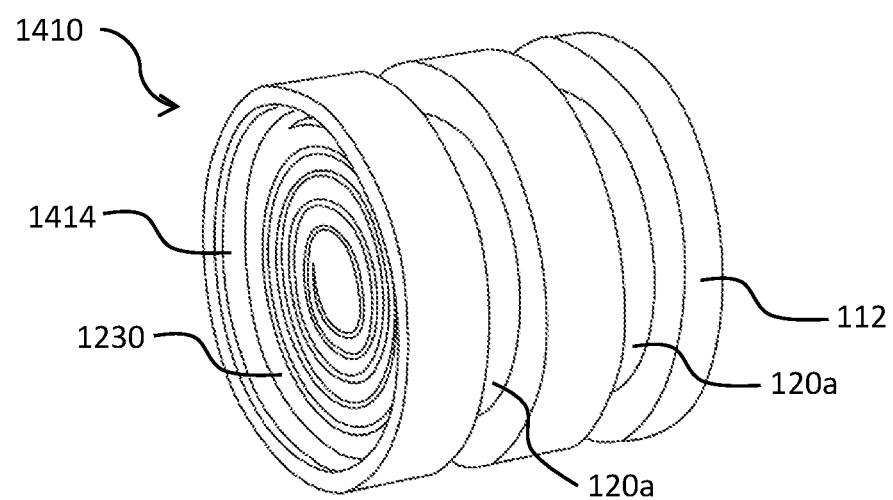
FIG. 10b is a perspective view of a pre-assembled valve.

FIG. 4 illustrates a valve 110, which may be used as the outlet valve 107 and/or the inlet valve 108. The valve 110 comprises a spherical valve member 111, and a valve seat member 112. The valve seat member 112 has a first recess 113. The first recess 113 may extend from a first end of the valve seat member 112, which preferably is cylindrical, towards an opposing second end. The first recess 113 may have a depth that is slightly smaller than a diameter of the spherical valve member 111, which may be used for biasing the spherical valve member 111 towards a valve seat 114 of the valve seat member 112, as will be discussed below. In other embodiments, such as illustrated in FIGS. 10a-10b, the spherical valve member 111 is fully contained in the valve seat member 112. The first recess 113 has a diameter slightly larger than the diameter of the spherical valve member 111. The spherical valve member 111 can freely move within the first recess 113 in the axial direction of the valve 110. However, the spherical valve member 111 can substantially not move within the first recess 113 in the radial direction of the valve 110. Hence, the spherical valve member 111 may be centered within the first recess 113. A slight space between the recess 113 and the spherical valve member 111 allows fluid to pass when pressurized, whereby the spherical valve member 111 moves in the axial direction of the valve to provide clearance from the valve seat 114. The valve seat member 112 has a second recess 115 from the second end, opposing the first end, of the valve seat member 112. The second recess 115 is preferably cylindrical. The second recess 115 is co-axial with the first recess 113 and has a diameter that is smaller than the diameter of the first recess 113. Hence, the valve seat 114 may have a diameter corresponding to a diameter of the spherical valve member 111, which is not the maximum diameter of the spherical valve member 111. The first diameter may be in the range of 1.5-3 mm. The second diameter may be in the range of 1-2 mm.

The valve seat 114 is formed by an edge at the intersection of the first recess 113 and the second recess 115. The edge forms a surface against which a portion of the spherical valve member 111 may be seated in a closed position of the valve. The edge may have a chamfer. The chamfer may have a curvature, which is substantially complementary in shape to the curvature of an outer surface of the spherical valve member 111. Hence, the surface contact between the spherical valve member 111 and the valve seat 114 may be increased. An increased surface contact is useful in applications wherein the amount of liquid to be administered is small and thus the compression in the chamber 104 for each increment of a piston 116 is low, such as for delivery of insulin. The increased surface contact improves the tightness of the valve, particularly in delivery of small amounts of fluid.

The spherical valve member 111 may be centered with the first recess 113 and the second recess 115, i.e. the center of the spherical valve member 111 is coaxial with the first recess 113 and the second recess 115 in the closed position. Since the diameter of the spherical valve member 111 is larger than the diameter of the second recess 115, a portion of the spherical valve member 111 extends into the second recess 115. The diameter and/or the length of the second recess 115 is/are dimensioned such that the portion of the spherical valve member 111 located therein does not reach the second end of the valve 110.

Returning to FIG. 3, at least one of the outlet valve 107 and the inlet valve 108 comprises a spherical valve member 111a, 111b, and a valve seat member 112a, 112b arranged between the first housing unit 102 and the second housing unit 103. The valve 110 of FIG. 4 may be as used as the outlet valve 107 and/or the inlet valve 108, respectfully. The valve 110 of FIG. 3 may also be used as the outlet valve 8 of the embodiments of FIGS. 1a-1f; and/or arranged in an inlet path to the inlet 9 of FIGS. 1a-1f. Hence, for embodiments of the outlet valve 107 and/or the inlet valve 108, reference is made to the embodiments illustrated in FIG. 4. The piston 116 may be arranged in the chamber 104, such as illustrated in FIG. 4. The piston 116 may be a reciprocating piston 116 for pressuring liquid contained in the chamber 104. The piston 116 may have a circumferential recess 117 at its distal end for receiving a seal, such as an O-ring, for sealing between the chamber 104 and the piston 116. In a forward stroke, the piston pressurizes the liquid in the chamber 104 when moved towards the valves 107, 108, which closes the inlet valve 108 and/or opens the outlet valve 107. In a backward stroke the piston 116 is moved away from the valves 107, 108, which closes the outlet valve 107 and/or opens the inlet valve 108 and the chamber 104 is refilled with fluid. Hence, the inlet valve 108 and outlet valve 107 may co-operate to prevent pressurizing the reservoir for the liquid and a back-flow of liquid already delivered via the outlet. If the valves 107, 108 are arranged at the inlet 9 and the outlet 7 of FIGS. 1a-1f, the valves may operate to build vacuum, as has been described above. In each of these embodiments, also when a single outlet valve 8 is used as described above with regard to FIGS. 1a-1f, the piston can be made smaller compared to the prior art, allowing for increased precision for delivering the same amount of liquid in a single step.

In some embodiments, the valve seat member 112 and at least one of the first housing unit 102 and the second housing unit 103 are made of different materials. For example, the first housing unit 102 and/or the second housing unit 103 may be made of a medical grade plastic material. A housing for the chamber 2 of the embodiments of FIG. 1a-1f may be made of such medical grade plastic material. The medical grade plastic material may have properties such that the housing unit may be sterilized, e.g. by hot or cold sterilization, and meet FDA (Federal Drug Administration) and USP (United States Pharmacopeia) classifications, such as for containing liquid medical medicaments and nutrients. Such plastic materials are generally available as such and will not be further discussed herein. The valve seat member 112 may be made of a metallic material, such as surgical steel, for example austenitic 316 stainless steel or martensitic 440 or 420 stainless steel. Such metallic materials are generally available as such and will not be further discussed herein. Providing the housing 100 and the valve seat member 112 in different materials provide for producing an infusion pump that is applicable for low pressures, and thus for delivery of small amounts of liquids in a single step, efficiently with high precision. Components of the infusion pump that are not critical for the accuracy of the infusion pump, such as the first housing unit 102, the second housing unit 103, and/or the piston 116 may be made in a material that can be produced in high volumes, such as by injection molding or casting, quickly and thus efficiently and at low cost. However, such materials and/or production processes may not have sufficient accuracy and/or be elastic making them unsuitable for achieving the accuracy required in certain applications, such as for administration of the amount of fluid involved e.g. for administration of insulin. The valve seat member 112 may be made of a material that is suitable for higher precision and/or producing using different technology than that of the housing 100. Such material may e.g. be a plastic material, for example the metallic material mentioned above. Plastic materials may be processed using one or several processing techniques, such as milling, turning, and/or punching, and using tools for successively increased accuracy of the components. Thereby, an interface between the valve seat member 112 and the spherical valve member 111 can be provided with higher accuracy compared to providing this interface directly in any of the housing units 102, 103 made of an elastic material. This is particularly useful in applications where the pressure in the chamber 104 for administrating the liquid is low. In applications where pressures in the chamber 104 are higher, the accuracy between the valve seat 114 and the spherical component is less critical. With high enough pressures, the valve seat 114 may be formed directly in the material of the housing 100, even if that is an elastic material. The valve seat member 112 forms an intermediate component increasing the accuracy of the interface between the valve seat 114 and the spherical valve member 111. Accuracy in this context means that the surface of the valve seat 114 and the outer surface of the spherical valve member 111 should be sufficiently smooth such that liquid may not pass the interface even when the piston 116 is moved a short distance within the chamber 104, such as in the range of 0.005-0.015 mm in each in increment of the piston 16.

The diameter of the chamber 2, 104 may be in the range of 3-8 mm. The maximum length of the chamber 2, 104 for containing liquid may be in the range of 3-20 mm. Hence, the chamber 2, 104 may, as well as the infusion pump as such, be made compact.

FIG. 3 illustrates the first housing unit 102 and the second housing unit 103, which may be provided separate from the valve members 107, 108. The housing comprises at least one recess 120a, 120b that forms a space for receiving at least one valve member 107, 108. In this embodiment, a first recess 120a is provided for receiving the outlet valve member 107. A second recess 120b is provided for receiving the inlet valve 8. A single recess may be provided in case the valve members 107, 107 are axially spaced apart. The first recess 120a and the second recess 120b may be sized such that the valves 107, 108 are received snugly therein in, for example in a press or friction fit. Hence, a seal is formed between the each recess 120a, 120b and the respective valve 107, 8. Thus, the recess 120a, 120b may have an inner dimension substantially corresponding to an outer dimension of the valve seat member 112a, 112b, whereby an outer surface of at least one of the outlet valve 107 and the inlet valve 108 is enclosed by each recess 120a, 120b.

In some embodiments, the space formed by the recess 120a, 120b is provided partially in the first housing unit 102 and partially in the second housing unit 103. This provides, e.g., for efficient assembly of the infusion pump. For example, about ⅓ to ⅔, such as about ½, of the recess may be formed in the first housing unit 102 and about ⅔ to ⅓, such as ½, of the recess may be formed in the second housing unit 103. Hence, the valve 107, 108 may first be arranged in the recess of the first housing unit 102, and then the second housing unit 103 is inserted into another recess at the distal end of the first housing unit 102, which is slightly larger in diameter than the recess in which the valve is arranged. Hence, the second housing unit 103 may form a plug, also illustrated in FIG. 6, received within the first housing unit 102 and may be positioned at least partially between the valve 107, 108 and a distal end of the housing 100, such as the distal end of the first housing unit 102. This provides for providing a seal between the first housing unit 102 and the second housing unit 103. Furthermore, the first housing unit 102 may be joined to the second housing unit 103 such that the valve 107, 108 is fully enclosed and the housing units 102, 103 may not disassemble and are fluid tight. Furthermore, a joint may be formed between the first housing unit 102 and the second housing unit 103, e.g. by an adhesive and/or by heat fusion of the material of the housing units 102, 103. At least one seal, such as an O-ring, may be provided in at least one recess of the valve seat member 112 and in abutment with the recess of the housing 100. In the illustrated embodiment, a first seal is arranged between the valve seat member 112 and the first housing member 102, and a second seal is provided between the valve seat member 112 and the second housing unit 103. An end of the second housing unit 3 is arranged between the seals in the axial direction of the housing 1 and within the first housing unit 102. Hence, efficient sealing is provided at the same time as the housing units 102, 103 and the valve 110 are easy to assemble.

In some embodiments, the first housing unit 102 and the second housing unit 103 are made of the same material. This provides for efficient production of these components, as described above, in a plastic material. It also provides for efficiently forming the joint, such as described above.

Figure 5:
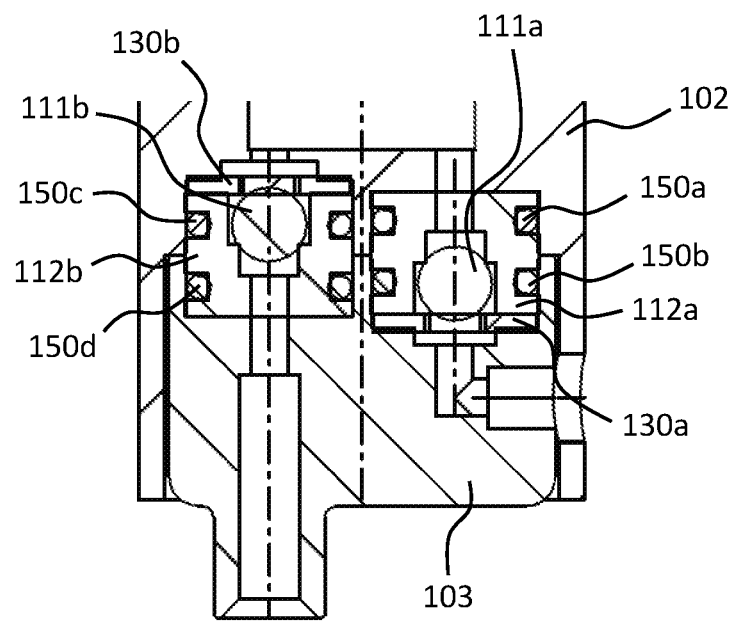
FIG. 5 is a cross-sectional view of an embodiment of an inlet valve and an outlet valve each arranged in a recess of a first housing unit and a second housing unit.
Figure 6:
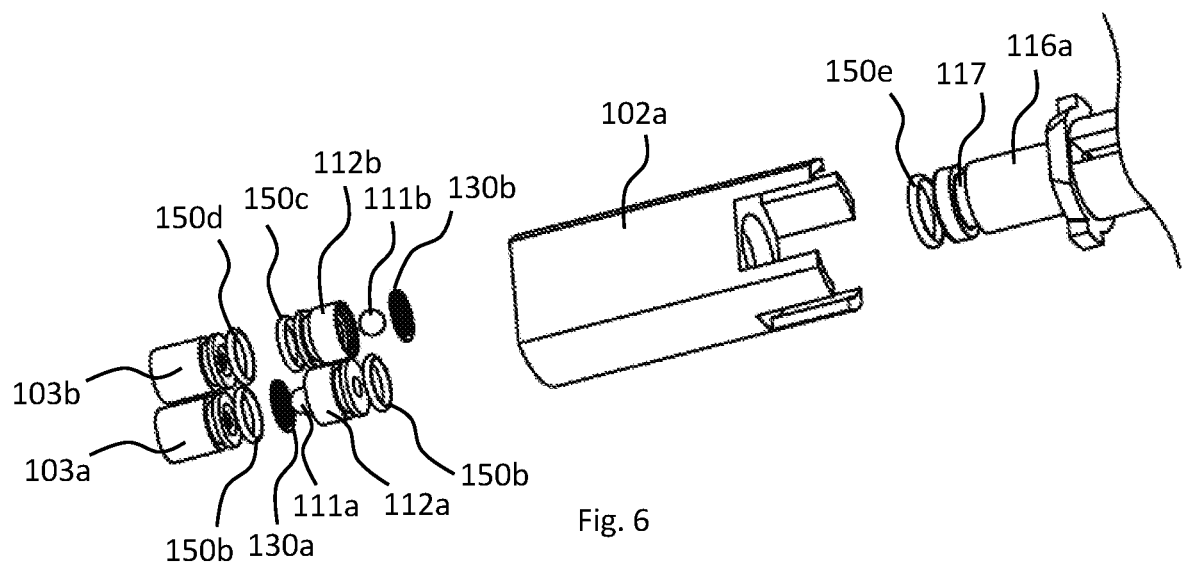
FIG. 6 is an exploded view of an embodiment of the infusion pump.

FIG. 5, illustrates embodiments of at least one spring member 130a, 130b that may be arranged within the housing 100 and in fluid communication with the chamber, such as between the first housing unit 102 and the second housing unit 103, illustrated e.g. also in FIG. 6. Each spring member 130a, 130b may be arranged to bias the spherical valve member 111a, 111b towards the valve seat 114 of each valve seat member 112a, 112b. A spring member 130a, 130b may be required when the amount of liquid that is administrated is small, i.e. when the length movement of the piston 116 is small for each increment, such as described above, whereby the pressure in the chamber 104 is equally small. Such biasing in not required for higher pressures and larger amounts of liquids being delivered each time of delivery.

In the embodiment of FIG. 3, the spring member 130a, 130b comprises a disc spring. The disc spring may be made of a plastic material, wherein the shape of the disc spring provides the required flexibility for biasing of the spherical valve member 111. In other embodiments, the spring member 130a, 130b is made of an elastic material, wherein the elastic properties of the spring member provide the flexibility of the spring element for the required biasing force.

FIG. 6 illustrates an embodiment of the infusion pump, including the housing with the first housing unit 102a. As illustrated, the first housing unit 102a may include a plurality of guide members at its proximal end for guiding the piston 116 during its reciprocating movement. The guide members extend substantially in the longitudinal axis of the first housing unit 102a. The piston 116a has mating protrusions extending substantially perpendicular to its longitudinal axis. Each protrusion is slidably received between a pair of guide members. Hence, guiding reciprocating movement of the piston 116 within the chamber along the longitudinal axis is provided for. An O-ring 150e is arranged circumferentially around the piston 116a at the circumferential recess 117. The valve seat members 112a, 112b may be arranged within the housing, such as within the first housing unit 102. In this embodiment, each valve seat member 112a, 112b has a single circumferential recess for receiving a seal member 150a, 150c, such as an O-ring. The spherical valve members 111a, 111b may be arranged as described above. The spring members 130a, 130b may be arranged as described with regard to each of the embodiments described herein.

Figure 9:
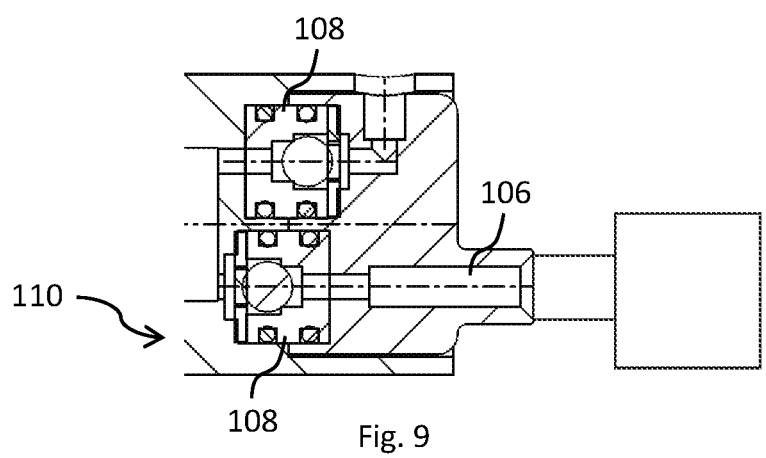
FIG. 9 is a cross-sectional view of a valve with an inlet connected to a reservoir.

In the embodiment of FIG. 6, the valve seat member 112a, 112b is arranged at a recess of the first housing unit 102a. The second housing unit 103a, 103b forms a plug. In the illustrated embodiment, the recess of the first housing unit 102a for each valve seat member 112a, 112b has a uniform diameter. Hence, a first plug 103a is provided for valve seat member 112a, and a second plug 103b is provided for the second valve seat member 112b. The diameter of the plugs 103a, 103b may correspond to the diameter of the valve seat members 112a, 112b, and may this be provided in the recesses between the valve seat members 112a, 112b and the distal end of the first housing unit 102a. Each plug 103a, 103b has a through hole that forms the inlet and the outlet, respectively. A seal member 150b, 150d, such as an O-ring, may be arranged in a circumferential recess in the plug 103a, 103b, which provides a seal between the first housing unit 102a, and the second housing unit 103a, 103b. The first plug 103a may be connected to a fluid conduit, such as a hose of an infusion set. Hence, a fluid tight conduit is provided between the chamber and the outlet of the infusion pump. Similarly, the second plug 103b may be connected to or form part of a reservoir, e.g. as illustrated in FIG. 9. Hence a fluid tight conduit is provided between the reservoir and the chamber. The embodiment of FIG. 6 provides for a production process that is simplified by providing multiple components with uniform diameters, which also facilitates the assembly process.

In other embodiments, the first and the second plug 103a, 103b are provided as a single unit, such as illustrated in FIGS. 3 and 4, and arranged relative the first housing unit 102a. Each plug 103a, 103b may form the purpose to secure the valve seat members 112a, 112b within the first housing unit 102, 102a. Additionally or alternatively, each plug may provide a seal, e.g. using the seal member 150b, 150d, between the first housing unit 102a and the second housing unit 103a, 103b. Hence, the tightness in the communication path from the inlet, via the chamber, to the outlet is further enhanced compared to having a single seal member only at the valve seat member 112a, 112b.

In still other embodiments, the housing only comprises the first housing unit 102, 102a. Any of the valve seat members 112a, 112b may be arranged in a recess of the first housing unit, such as described above, and provide the inlet and/or the outlet, respectively. The embodiment of FIG. 6 may also be combined with the other embodiments described herein, e.g. with regard to the spring members 130a, 130b, the seal members 150a-150d, and the first housing unit 102 and the second housing unit 103.

Figure 7:
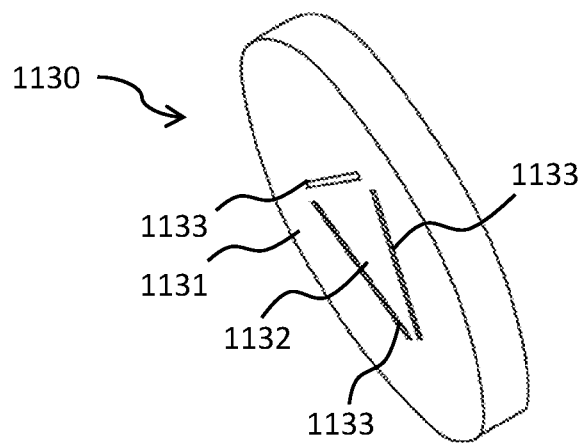
FIG. 7 is a perspective view of an embodiment of a spring member.
Figure 8:
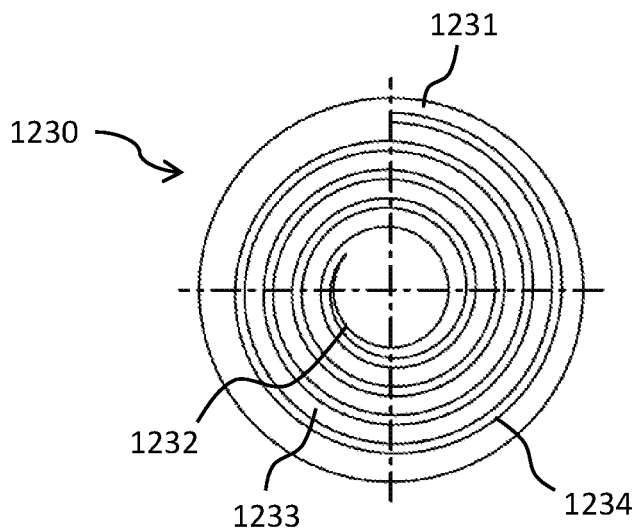
FIG. 8 is a top view of an embodiment of a spring member.

FIGS. 7-8 illustrate embodiments of the spring member 1130, 1230 that comprises a rim 1131, 1231 such as a circumferential rim. The rim 1131, 1231 may be arranged at least partially around the spherical valve member 111, such as illustrated in FIG. 5. The spring member 1130, 1230 may have a pressure component 1132, 1232 that is arranged at the center of the spring member 1130, 1230, and that may be arranged in abutment with the spherical valve member 111. Hence, the pressure component 1132, 1232 may form a seat for the spherical valve member 111. The pressure component 1132, 1232 may abut the spherical valve member 111 coaxially with recesses 114, 115 of the valve seat member 112. A spring element 1133, 1233 connects the pressure component to the rim 1131, 1231. The spring member 1130, 1230 may be generally disc shaped. Hence, the rim 1131, 1231, the pressure component 1132, 1232, and the spring member 1130, 1230, may be provided in a single plane. As such, the spring member 1131, 1230 may form a disc spring.

Furthermore, the spring member 1130, 1230 may be formed from a single piece of material.

The spring member 1130, 1230 can be used for a valve 110 that is efficient to assemble while being useful for delivery of small amounts of liquid where the pressure provided by the piston 116 is not sufficient for providing a tight interface between the valve seat 114 and the spherical valve member 111. Particularly, the embodiments of FIG. 7-8 provide for applying a small pressure, such as a few hg, to the spherical valve member 111. Such small pressures are difficult to provide with a helical spring having subsequent turns in separate planes. Furthermore, a disc shaped spring member is easy to assemble with the valve seat member 112a, 112b, such as will be discussed below.

FIGS. 7 and 8 illustrate embodiments where the rim 1131, 1231 is arranged completely around the spring member 1130, 1230, such as circumferentially around the spring member 1130. Hence, it may also be provided circumferentially around an end of the valve seat component 112, such as is illustrated in FIGS. 10a-10b.

The rim 1131, 1231 may form a seal between the valve seat member 112 and at least one of the first housing unit 102 and the second housing unit 103, such as when the rim 1131, 1231 is provided in an elastic material. For the outlet valve 107, the rim 1131, 1231 may be arranged between the valve seat member 130a and the first housing unit 102. For the inlet valve 108, the rim 1131, 1231 may be arranged between the valve seat member 130b and the second housing unit 103.

In the embodiments of FIG. 7, the spring element 1130 is formed by at least one slit 1133 in an elastic element. The rim 1131 may be provided circumferentially around the slit 1133. The spring member 1130 may be cylindrical, such as disc shaped. The elastic element may provide a seal, such as by the rim that encircles the at least one slit. The spring member 1130 and the seal member may be formed as a single component. A central portion of the spring member 1130 may form the pressure component 1132. The pressure provided by the spring member 1130 may e.g. be adjusted by the type of material of the spring element 1133, the thickness of the material, and the number and/or shape of the at least one slit. The at least one slit may also be arranged for efficient flow of liquid passing the spherical valve member 111. In this embodiment, three slits 1133 are arranged in a triangular patter, with a piece of material separating the vertices of the triangle. Hence, the pressure component 1132 is provided at the center of the triangular slit pattern.

In other embodiments, the at least one slit 1133 is semi-circular. Alternatively or additionally, the slit may be straight extending from one side of the rim 1131 to the other side of the rim 1131. A straight slit allows for uniform pressure applied on a spherical valve member 111, which in turn provides for accuracy, particularly for delivery of small amounts of liquid. The number of and/or length/width of the slits provided may be selected depending on pressures, amount of liquid to be delivered, biasing force, the material of the spring member 130 etc. For example, the length may be in the range of 0.5-4 mm.

The embodiment of FIG. 8 illustrates a spring member 1230 in the form of a disc spring, which may be used for a valve of an infusion pump as discussed above. The disc spring comprises the rim 1231, the spring element 1233, and the pressure component 1232 in the center of the disc spring. The pressure component 1232 forms in this embodiment a circumferential seat. The spring element 1233 is arranged around the circumferential seat, and the rim 1231, the spring element 1233, and the circumferential seat are arranged in a single plane.

In the illustrated embodiment, the rim 1231 is ring-shaped, the spring element 1233 is spiral winding and extends from the rim 1231 to the circumferential seat. The spring element 1233 may have a plurality of circumferential turns. The thickness of the spring element 1233 may be smaller than the width of each turn or the pattern such that the force exerted by the spring element 1233 is substantially in the axial direction of the spring member 1230. Furthermore, the circumferential seat is substantially circular. In this embodiment, the helically shaped spring element 1233 has a first end connected to the rim 1231, and a second free end. The last turn of the helically shaped spring element 1233 forms the circumferential seat. In other embodiments, the circumferential seat is ring shaped, to which the second end of the spring element 1233 is connected. Furthermore, in other embodiments, the rim 1233 is formed by the last turn of a winding spring element. Hence, the entire spring element 1233 may be winding in a single plane. At least a first turn may form the rim 1231, and a last turn may form the circumferential seat. Between the rim 1231 and the circumferential seat, there may be distances between each turn at least when assembled in the valve, such that liquid is allowed to pass.

In the embodiment of FIG. 8, the spring element 1233 is formed by at least one slit 1234 extending from the rim 1231 to a center section of the spring member 1230. Again, the rim 1231 may be provided circumferentially around the slit 1234. The spring member 1230 may be cylindrical, such as disc shaped. A central portion of the spring member 1230 may form the pressure component 1232. The pressure provided by the spring member 1230 may e.g. be adjusted by the type of material of the spring member 1230, the thickness of the material, and the number and/or shape of the at least one slit. The spring member 1230 may be made of a metallic material, such as spring steel. The at least one slit 1234 may also be arranged for efficient flow of liquid passing the spherical valve member 11. In this embodiment, the slit 1234 is a spiral slit that forms a spiral spring element 1233. The spring element may form one or several turns. In the illustrated embodiment, the spring element forms almost four turns, but may be in the range of 3-6 turns. The thickness of the spring member 1230, the width of the spring element 1233, and the shape of the spring element 1233 may adjust the spring coefficient of the spring member 1230. In the illustrated embodiment, the spring element 1233 ends a distance in the radial direction from the center of the spring member 1230. The last turn of the spring element 1233 at the center of the spring member may form a substantially circular ridge that forms the pressure component 1232. The ridge may have a diameter that is smaller than the maximum diameter of the spherical valve member 11 such that a pressure is applied around the spherical valve member 11, as is illustrated in FIG. 10a. In other embodiments, the spring element 1233 connects the rim 1231 to the pressure component 1232 in the form of a ring shaped element with a diameter that is smaller than the maximum diameter of the spherical valve member 111. In still other embodiments, the pressure component 1232 is a plate arranged at the center of the spring member 1230.

In other embodiments, the at least one slit 1234 forms a meandering pattern between the rim 1231 and the pressure component 1232. In still other embodiments, the at least one slit 1234 forms a cell structure between the rim 1231 and the pressure component 1232.

The spring member 1130, 1230 may be arranged to bias the spherical valve member 111 towards the valve seat 114. The pressure component 1132, 1232 may be biased towards the spherical valve member 111 by fixing the rim 1131, 1231 in an appropriate position relative the spherical valve member. For example, the rim 1131, 1232 may be arranged between the valve 111 and the first housing unit 102 and/or the second housing unit 103, and the pressure component to abut the spherical valve member 111 with a desired biasing force towards the valve seat 114. The at least one slit 1133, 1234 allows for movement of the spherical valve member 111 and for liquid to pass through the spring member 1130, 1230.

As is illustrated in FIG. 4, the rim 1131 may be arranged at a ledge 140 of the recess 120a, 120b of the housing 101. For example, the ledge 410 may have a width that substantially corresponds to a width of the end of the valve seat member 112 at its first recess 113. The rim 1131, 1231 may be fixed between the housing 101 and the valve seat member 112a, 112b by applying a pressure to the valve seat member 112a, 112b, such as by applying a pressure to the second housing unit 103 when assembled with the first housing unit 102. Hence, efficient assembly of the spring member 130 is provided for. Furthermore, the efficiency may be further improved by providing a seal with the spring member 130.

A height of the ledge 140 in the longitudinal direction of the valve seat member 111 may be shorter than a thickness of the rim 1131. This ascertains that a pressure may be applied to the spring member 1130, 1230 when the valve seat member is assembled in the housing 101. Furthermore, if the spring member 1130 is an elastic spring member the height of the ledge 140 may be shorter than the thickness of the rim 1131 in an uncompressed state. In FIG. 4, the rim 1131 is illustrated in its uncompressed state for illustration purposes such that the ledge 140 and the rim 1131 overlap. However, the rim 1131 would be compressed when the components are assembled. When the components are assembled, the valve seat member 111 is assembled in the housing 101 such that it abuts the ledge 140, whereby the rim 1131 is compressed a predefined amount, which may provide a seal. At the same time, the pressure component 1132 is biased towards the spherical valve member 111 providing a seal between the spherical valve member 111 and the valve seat 114. The same principle for providing biasing applies even if the spring member 1130, 1230 is provided in a non-elastic material, such as the embodiment of FIG. 8. For example, the valve seat member 112 may compress the rim 131 when the second housing unit 103 is arranged relative the first housing unit 102 in an assembled state.

As can be seen in FIGS. 5 and 6, at least one seal member 150a, 150b may be provided between the first housing unit 102, 102a and the valve seat member 112a of the outlet valve 107. Correspondingly, at least one seal 150c, 150d may be provided between the second housing unit 103 and the valve seat member 112b of the inlet valve 108, or the between the first housing unit 102a and the second housing unit 103a, 103b, such as has been described above.

The infusion pump is described above, which may comprise at least one of the outlet valve 107 and the inlet valve 108. The outlet valve 107 and the inlet valve 108 may be identical, but oriented differently in the housing 101. The outlet valve 107 may arranged with its spherical valve member 111a towards the outlet 105. The inlet valve 108 may be arranged with its spherical valve member 111b towards the inlet 106. The outlet 105 and the inlet 106 may be provided in at least one of the first housing unit 102 and the second housing unit 103. In the embodiments of FIGS. 3 and 6, the inlet 106 is provided entirely in the second housing unit 103, whereas the outlet 105 is formed partially in the first housing unit 102 and partially in the second housing unit 103. Furthermore, the inlet valve may be arranged at the inlet 9 and axially arranged at the side surface of chamber 2, preferably at the proximal end of the chamber 2, as has been described above with regard to FIGS. 1a-1f.

In some embodiments, the valve seat member 111a of the outlet valve 107 and the valve seat member 111b of the inlet valve 108 are provided as a single unit. The first recess 113 and the second recess 115 are provided in a single component, such as a disc shaped element, for each of the outlet valve 107 and the inlet valve 108. This provides for efficient assembly of the infusion pump, wherein the number of components is reduced. A single component may comprise both an inlet valve seat member and an outlet valve seat member. For such an arrangement, a seal may be provided on each side of the single component, which comprises a spring member for biasing the spherical valve member 111a, 111b on each side. A seal may also be shaped for sealing between the outlet 105 and/or inlet 106 and the single component, which may be formed as an integral unit with the spring member, wherein efficient assembly of the infusion pump is provided for.

Embodiments provide a combined seal and spring member. In some examples, such embodiments are used with an infusion pump according to the invention. The combined seal and spring member may be arranged between the valve seat member 111 and at least one of the first housing unit 102 and the second housing unit 103 of the infusion pump.

Embodiments provide a method for providing an infusion pump according to the embodiments described above. The method comprises providing the first housing unit 102, which comprises at least a portion of the chamber 104 located therein. Also, the second housing unit 103, which may have the outlet 105 and/or the inlet 106, is provided. Furthermore, the outlet valve 107, which may include a first spherical valve member 111a and a first valve seat member 112a, may be provided. The inlet valve 108, which may include a second spherical valve member 112a and a second valve seat member 111b may, be provided. The outlet valve 107 may be arranged between the chamber 2, 104 and the outlet 105 in a first space formed by the first housing unit 102 and the second housing unit 103, such as described above. The inlet valve 108 may be arranged between the inlet 6 and the chamber 2, 104 in a second space, such as formed by the first housing unit 102 and the second housing unit 103 or between the chamber 2 and the reservoir.

In the embodiments described above, the housing 101 is described as comprising a first housing unit 102 and a second housing unit 103 that are provided as separate units that are assembled after the valves 107, 108 are arranged in the first housing unit 102. In other embodiments, the housing is made as a single unit, such as by molding the housing 1 around the other components, for example the outlet valve 107 and inlet valve 108.

In some embodiments, the infusion pump comprises the housing 101, the chamber 2, 104 located in the housing 101, the outlet 7, 105, the outlet valve 107 between the chamber 2, 104 and the outlet 105. It may also comprise the inlet 6, 9. Optionally, it may also comprise the inlet valve 8 between the inlet 6, 9 and the chamber 2, 4. At least one of the outlet valve 107 and the inlet valve 108 may comprise a spherical valve member 111a, 111b and a valve seat member 112a, 112b, arranged in the housing. The spring member 130 may be arranged in the housing 101 and to bias the spherical valve member 111a, 111b towards the valve seat 114 of the valve seat member 112a, 112b. The spring member 130, 1130, 1230 may be arranged as has been described above with regard to the embodiments of FIGS. 3-8. These embodiments are particularly useful for embodiments of the infusion pump wherein the pressure provided within the chamber 2, 104 is low, and the amount of liquid distributed by moving the piston 6, 116 within the chamber 2, 104 is small.

In the embodiments presented herein, for example, the piston 6, 116 may only move a fraction of the length of the chamber 2, 104 for delivery of a predefined amount of the liquid, such as 0.00010-00050 ml, e.g. about 2.00025 ml. Thus, the buildup of pressure is low when liquid is ejected from the chamber 2, 104. When the chamber 2, 104 is to be re-filled, the piston 6, 116 may travel with a complete stroke, possibly even faster than when the liquid is ejected. Therefore, depending on the distance and/or speed the piston is travelling for delivery of a predefined amount of liquid, it may be desired to bias the spherical valve member 111b for the inlet valve 108. However, it may not be required to bias the spherical valve member 111a for the outlet valve 8, 107 such as when the inlet is arranged at the side surface of the chamber 2, 104. In other embodiments, the piston 6, 116 moves slowly during the inlet phase, wherein it may be desired also to bias the spherical valve member 111a for the outlet valve 8, 107. In still other embodiment, such as described above with regard to FIGS. 3-8, it may be desired that neither the spherical valve member 111a for the outlet valve 8, 107 nor the spherical valve member 111b for the inlet valve 108 are biased.

The spring member 130, 1130, 1230 may be configured as has been described above with regard to FIGS. 3-8, and be arranged in the housing 101, such as described above with relative to the first housing unit 102 and the second housing unit 103. The spring member 130, 1130, 1230 may be formed as a single integral component providing a seal, such as described above, and may thus be a component made of an elastic material. Alternatively, the seal and the spring member 130, 1130, 1230 are provided as separate components.

The spring member 130, 1130, 1230 may comprise the rim 1131, 1231 as described above. The rim 1131, 1231 may be arranged at a ledge 140, also as described above.

In embodiments using the spring member 130, the housing 101 may be made in the same material as the valve seat member 111, such as described above. In other embodiments, the valve seat member 111 and at least one of the first housing unit 102 and the second housing unit 103 are made of different materials, such as described above. The spring member 130, 1130, 1230 may be made of a third material, that is more elastic than the material of the housing. The material of the housing may be plastic.

The spherical valve member may be made of a plastic material, such as a metallic or a ceramic material.

FIG. 9 illustrates the inlet 106 of the infusion pump according to the embodiments described above arranged in fluid communication with a reservoir for a liquid medicament or a nutrient. When not otherwise described, aspects described with reference to the valve 110 and its arrangement within the housing 101 of the infusion pump, such aspects are applicable to any of the outlet valve 107 and the inlet valve 108. The reservoir may have an arbitrary shape and may be collapsible. The inlet may be arranged between the reservoir and the chamber 2.

Still alternative embodiments provide a method for providing an infusion pump. Such alternative methods includes providing a housing comprising a chamber 104, an outlet 105, and an inlet 106; providing an outlet valve 107, optionally comprising a first spherical valve member 111a and a first valve seat member 112a, which may comprise a first valve seat 114; optionally providing an inlet valve comprising a second spherical valve member 111b and a second valve seat member 112b, which may comprise a second valve seat 114; optionally providing at least one spring member 130, 1130, 1230; optionally arranging the outlet valve 107 between the chamber 104 and the outlet 105; optionally arranging the inlet valve 108 between the chamber 104 and the inlet 106 or between the reservoir and the inlet and at a side surface of the chamber 2, or only providing an inlet at the side surface of the chamber 2 without any inlet valve; biasing at least one of the first spherical valve member 111a towards the first valve seat 112a and the second spherical valve member 111b towards the second valve seat 112b using the at least one spring member 130, 1130, 1230.

The method may comprise arranging the spring member 130, 1130, 1230 as has been described above with regard to FIGS. 3-9.

In still other embodiments, the valve 110 may be provided as a pre-assembled component that may be produced and tested separately before assembly with the other components of the infusion pump.

FIGS. 10a-10b illustrate embodiments of a pre-assembled valve 1410 that comprises a spherical valve member 111, a valve seat member 112, and a spring member 1230. The spring member may be seated at a ledge 1413 formed at a proximal end of a recess 1414 at one end of the valve seat member 112. The spherical valve member 111 is arranged at least partially between the ledge 1413 and the valve seat 114. The valve seat 114 may be arranged at a distal end of the recess 1414. A small portion of the spherical valve member 111 extends between the end of the valve seat member 112 and the ledge 1413 such that it is biased towards the valve seat 114, as has been discussed before. The diameter of the recess 1414 at its proximal end may be slightly smaller than the remaining portion of the recess towards the ledge 1413, whereby at least one flange 1415 is provided at the proximal end of the valve seat member 112. The flange 1415 may extend towards the central longitudinal axis of the recess 1414 and have a minimum diameter slightly smaller than a maximum diameter of the spring member 1230. Hence, the spring member may be secured in the recess 1414 between the ledge 1413 and the flange 1415. The spring member 1230 is illustrated as spiral, but may have other shapes as discussed above. In the illustrated embodiments, the valve seat member 112 has two circumferential recesses for receiving seal members 150a, 150b (not illustrated), such as O-rings, to seal against the first and/or the second housing member 12, 13, such as described above. In other embodiments one, more than two, or no such recesses are provided. Providing the valve 1410 as a pre-assembled component provides for efficient assembly of the infusion pump. The valve 1410 may be a critical component for the functioning of the infusion pump. Hence, when provided as a separate component, it may be quality tested before assembly with the other components. That means that only approved valves are assembled with the other components. Hence, the scrap compared to performing the quality testing after assembly with the housing components may be reduced. Hence, an overall more efficient assembly of the infusion pump is provided for. Furthermore, it may be produced with productions techniques, such as milling, which is more accurate than production techniques used for the housing.

The infusion pump of the embodiments of presented above may be contained in an infusion pump device, such as an insulin pump. The piston 6, 116 may be connected to a motor, such as a step motor or a piezo motor, which is controlled by various electronics and one or several controllers or processors. The motor may move the piston 6, 116 in at least one step for delivery of a pre-defined amount of liquid, such as a fraction of a unit of insulin. The length of movement of the piston is dependent on the size of the chamber 2,104, which is fixed, and the amount to be delivered, which is variable. The amount to be delivered may be set in a user interface, and controller software may control the length of travel of the piston 14. Software instructions for the controller or processor may be stored in a memory. The controller or processor software instructions may also be configured to control an amount of liquid in the chamber 2, 104, in order to re-fill the chamber 2, 104 at defined intervals, such as when a particular amount of liquid has been delivered between two-refills of the chamber 2, 104, or when a minimum amount of liquid in the chamber 2, 104 has been reached.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

The invention claimed is:

1. An infusion pump, comprising:
 a chamber having a distal end and a proximal end, and a longitudinal axis between said proximal end and said distal end;
 a piston arranged for reciprocating movement within the chamber and along the longitudinal axis;
 at least one outlet from the chamber having an outlet valve; and
 at least one inlet into the chamber;
 wherein the at least one outlet and the at least one inlet are axially spaced apart along said longitudinal axis of said chamber,
 where the piston comprises a plurality of sealing members axially spaced apart and arranged to provide a seal between said piston and side surface of said chamber,
 wherein said plurality of sealing members comprises a first sealing member and a second sealing member, and wherein an axial distance between the first sealing member and the second sealing member is larger than a maximum movement of the piston within the chamber; and
 wherein the first sealing member is configured to be axially positioned distal of the inlet in a delivery phase of said infusion pump and the second sealing member is configured to be axially positioned proximal of the inlet in the delivery phase of said infusion pump, and the first sealing member and the second sealing member are configured to be at least partly axially positioned proximal of the inlet during a re-filling phase of said infusion pump.

2. The infusion pump according to claim 1, wherein said infusion pump is operable with a compression phase during which fluid in said chamber is delivered through said at least one outlet, and the re-filling phase, during which said chamber is re-filled with fluid through said at least one inlet, and wherein said piston has at least one axial position within said chamber overlapping an axial position of said at least one inlet into said chamber in said delivery phase to prevent fluid entering into said chamber.

3. The infusion pump according to claim 1, wherein said infusion pump is operable with the re-filling phase, during which said chamber is re-filled with fluid through said inlet, and wherein said piston is configured to have at least one axial position within said chamber at least partially non-overlapping said axial position of said at least one inlet in said chamber, said at least one inlet in said axial position of said piston configured to be at least partially exposed to said chamber in said re-filling phase to allow fluid entering into said chamber.

4. The infusion pump according to claim 1, wherein in a first time period of the re-filling phase, the outlet valve is configured to be closed and said piston configured to be axially overlapping said at least one inlet to build vacuum in said chamber during movement of said piston towards said proximal end, and wherein in a second time period of said re-filling phase said piston is configured to be at least partially axially non-overlapping said at least one inlet.

5. The infusion pump according to claim 1, wherein the chamber is cylindrical, the at least one outlet is axially arranged at the distal end of said chamber, and the at least one inlet is axially arranged at a side surface of said chamber.

6. The infusion pump according to claim 1, wherein the at least one inlet comprises a plurality of inlets.

7. The infusion pump according to claim 6, wherein the inlets are radially spaced apart within said chamber.

8. The infusion pump according to claim 6, wherein the inlets are axially aligned within said chamber.

9. The infusion pump according to claim 1, wherein the piston has an end surface with a beveled circumference, and wherein the beveled circumference is configured to be axially aligned with the at least one inlet during the re-filling phase of said infusion pump.

\* \* \* \* \*